United States Patent [19]
Duckett et al.

[11] Patent Number: 5,378,433
[45] Date of Patent: Jan. 3, 1995

[54] SAMPLE TUBE RACK AND ADAPTER

[75] Inventors: G. Scott Duckett, Raleigh; Michael L. Bishop, Chapel Hill, both of N.C.

[73] Assignee: Akzo N.V., Arnhem, Netherlands

[21] Appl. No.: 152,011

[22] Filed: Nov. 15, 1993

[51] Int. Cl.⁶ ............................ B01L 3/02; A47F 7/00
[52] U.S. Cl. .................................. 422/100; 422/102; 422/104; 436/809; 435/809; 211/601; 206/443
[58] Field of Search ...................... 422/102, 104, 100; 436/809; 435/809; 211/60.1, 74; 206/443

[56] References Cited
U.S. PATENT DOCUMENTS 3,679,129  7/1972  Livshitz et al. .................. 233/26
5,186,339  2/1993  Heissler ........................... 211/74

OTHER PUBLICATIONS

Allied Fisher Scientific "86" Catalogue p. 209, 1986.

Primary Examiner—James C. Housel
Assistant Examiner—David Redding
Attorney, Agent, or Firm—Spencer, Frank & Schneider

[57] ABSTRACT

A sample rack with at least one receptacle for the accommodation of respective sample tubes. At least one receptacle has a removable adapter sleeve located within it for receiving a corresponding sample tube. Additionally, locking means are included for fixedly engaging the adapter sleeve within the corresponding receptacle.

20 Claims, 3 Drawing Sheets

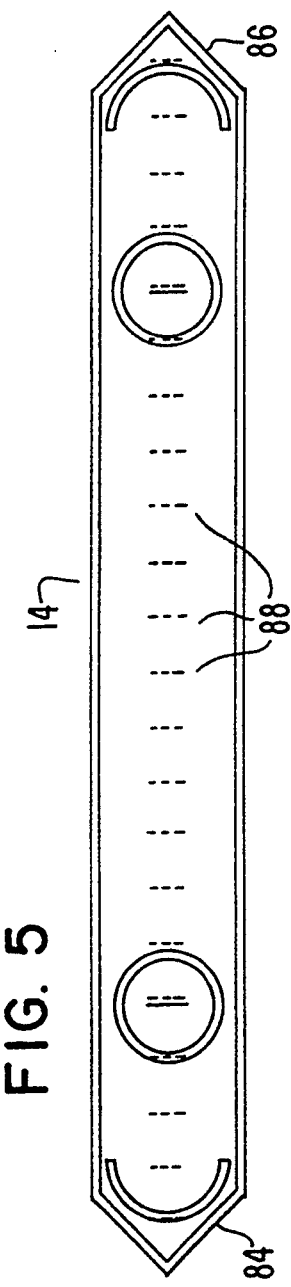
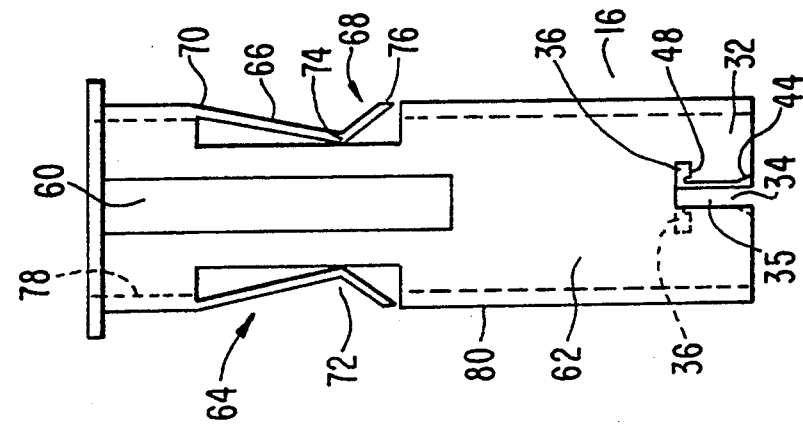
FIG. 5
FIG. 4
FIG. 2

SAMPLE TUBE RACK AND ADAPTER

CROSS REFERENCE TO RELATED APPLICATIONS

This application is related to the following U.S. patent applications, the disclosures of which are incorporated herein by reference:

(1) Ser. No. 07/833,950, to Hulette et al, entitled "Temperature Regulation in a Sample Handling System for an Optical Monitoring System", now U.S. Pat. No. 5,236,666, which is a continuation-in-part of U.S. patent application Ser. No. 07/443,951, now abandoned;

(2) Ser. No. 07/443,952, to Swope et al, entitled "Multichannel, Optical Monitoring Systems" now U.S. Pat. No. 5,002,392;

(3) Ser. No. 07/443,956, to Karp et al, entitled "Sample tube and Linear Drive Mechanism Therefor" now U.S. Pat. No. 5,040,894; and (4) Ser. No. 07/443,954, to Hoffman et al, entitled "Apparatus and Method for Cleaning Reagent Delivery Probes" now U.S. Pat. No. 4,989,623.

BACKGROUND OF THE INVENTION

The present invention relates to a sample tube rack assembly for holding, positioning and transporting sample tubes in an automated sample handling system.

Automated sample handling systems are known which automatically dispense patient fluid samples, such as blood plasma, along with reagents and other additives, into the reaction well of a cuvette which is then automatically positioned for monitoring or performing tests on the fluid sample. For example, in U.S. application Ser. No. 07/833,950, now U.S. Pat. No. 5,236,666, to Hulette et al, entitled "Temperature Regulation in a Sample Handling System for an Optical Monitoring System", there is disclosed an automated sample handling system for an optical evaluation instrument that can handle a high throughput of patient samples with a high degree of versatility, adaptability and reliability. The invention according to Hulette et al allows for walk-away automation for a sample handling system, once sample tubes containing patient samples are loaded into the system.

Accurate positioning and stabilizing of the sample tube within an automated system is essential. For example, in the aforementioned system disclosed by Hulette et al, a sample tube is advanced to a piercer where a piercing probe is caused to pierce the septum of the sample tube. A sample probe is lowered a predetermined distance into the sample tube to aspirate a programmed amount of sample. The sample probe is then removed from the sample tube and the sample subsequently dispensed into a cuvette.

However, sample tubes are manufactured in various brands and sizes having diverse parameters. For example, sample tubes manufactured by Beckton Dickinson of Rutherford, N.J. and sold under the brand name of Vacutainer with Hemogard Closure typically have a length of 75 mm and a diameter of 13 mm. In contrast, sample tubes made by Sarstedt and sold under the brand name of Monovette Microtainer can have a length of 65 mm and a diameter of 12 mm. Further, sample tubes may have different sizes depending on their particularly designed purpose. For example, the Monovette Microtainer brand sample tubes can have a length ranging from 65 mm to 92 mm. Consequently, the aforementioned automated systems typically are limited to using one standard size of sample tube for all tests and procedures to be run or by requiring that all of the sample tubes of a particular transport rack be of the same size. However, this latter option requires that expensive sensors and software be used to signal to the system the type of sample tubes contained within the rack so that the system "knows" when the sample tube has been pierced. Further, sample tube racks typically have several receptacles for holding several corresponding sample tubes. Requiring that all sample tubes of a particular rack be of the same size may result in empty receptacles within a rack being transported through the system, thereby decreasing the overall efficiency and flexibility of the system.

SUMMARY OF THE INVENTION

It is an object of the present invention to avoid the above-mentioned drawbacks by providing a sample rack with a removable adapter sleeve, so that different diameter and length sample tubes may be used simultaneously within the sample rack.

It is a further object of the invention to provide a sample rack that prevents movement of the sample tubes accommodated within the rack.

It is yet another object of the present invention to provide a sample rack that accurately positions various sized sample tubes at a standard location.

The above and other objects are accomplished according to the invention by the provision of a sample rack assembly including a sample rack having at least one receptacle for receiving a respective sample tube; at least one adapter sleeve removably insertable into a receptacle, the adapter sleeve receiving a corresponding sample tube; and locking means for releasably locking the adapter sleeve within a corresponding receptacle.

The invention will be described below in greater detail in connection with an embodiment thereof that is illustrated in the drawing figures.

BRIEF DESCRIPTION OF THE DRAWINGS

The foregoing objects and advantages of the invention, together with other objects and advantages which may be attained by its use, will become more apparent upon reading the following detailed description of the invention taken in conjunction with the drawings. In the drawings, where like reference numerals identify corresponding components:

FIG. 2 is an elevational view of a preferred embodiment of an adapter sleeve according to the present invention.

FIG. 4 is a plan view of the sample rack of FIG. 3 when used as a stand.

FIG. 5 is a plan view of the shuttle tray of the present invention.

DETAILED DESCRIPTION OF THE INVENTION

Figure 1:
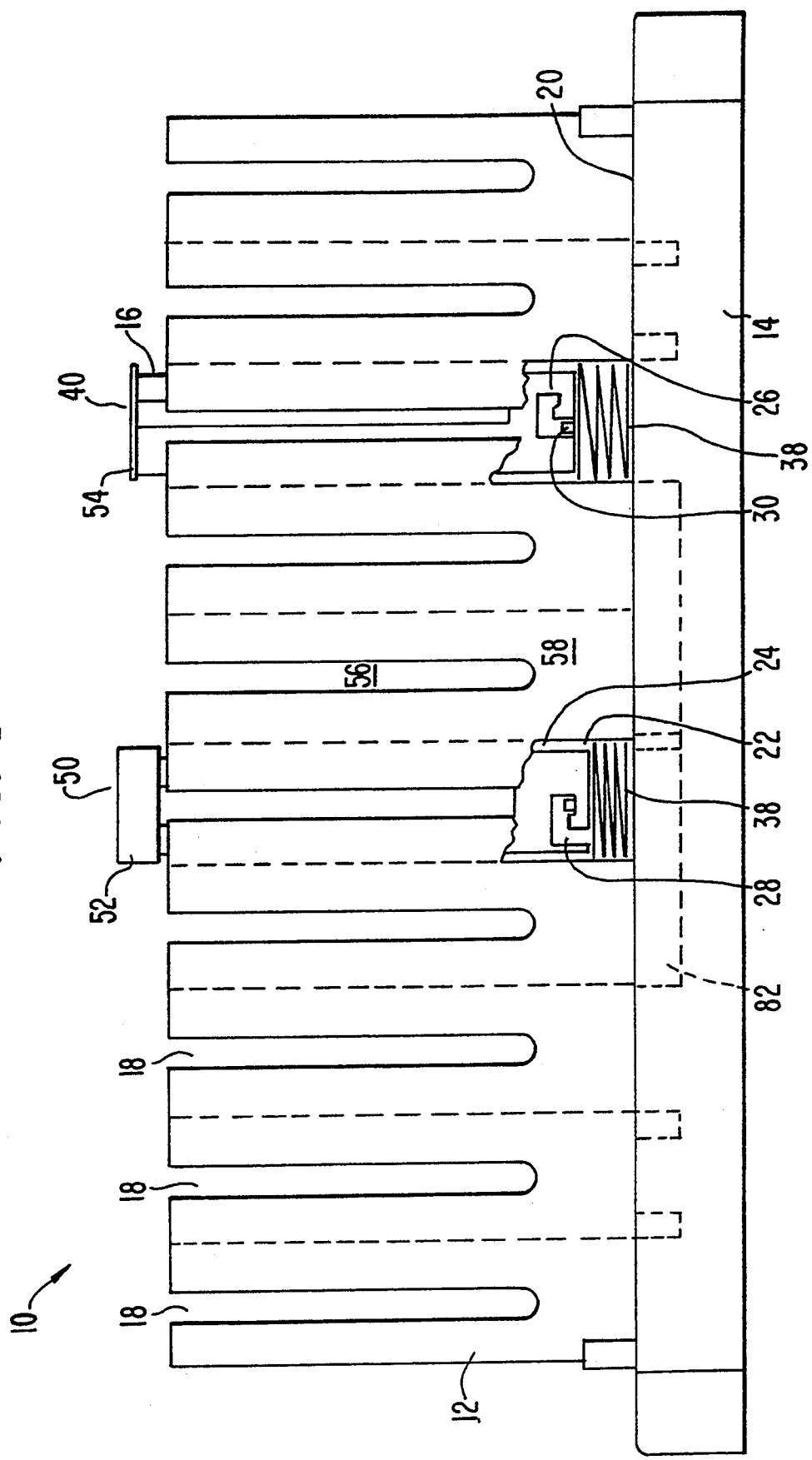
FIG. 1 is an elevational view of a preferred embodiment of the present invention illustrating the shuttle tray, adapter sleeves, and a partial sectional view of the sample rack.

Referring to FIGS. 1 and 2, a sample rack assembly 10 for transporting, holding and positioning sample tubes is illustrated. In this context, the term "sample"

can include, for example, any fluid or substance, such as human fluids, i.e. serum, blood, urine, cerebral spinal fluids, or test reagents.

Typically, sample rack assembly 10 includes a sample rack 12, a shuttle tray 14 and at least one adapter sleeve 16. Sample rack 12 is provided with at least one receptacle 18 for the accommodation of sample tubes and associated adapter sleeves. Preferably, several receptacles 18 are arranged in a linear direction, so that sample rack 12 has an essentially rectangular shape. Of course, sample rack 12 can have other shapes. For example, carousel type transporting systems are known where it may be desirable to use a sample rack 12 having either one receptacle, or several receptacles arranged so that sample rack 12 has an arcuate shape.

Each receptacle 18 has a receptacle base 20, a receptacle base portion 22 adjacent to the receptacle base, and a receptacle upper portion 24 adjacent to the receptacle base portion. Typically, each receptacle 18 extends in a vertical direction, so that the sample tubes are carried by rack 12 in an upright position.

Adapter sleeve 16 has a shape, preferably tubular, which corresponds to the shape of the interior of receptacle 18 so that adapter sleeve 16 can easily slide into and out of its corresponding receptacle 18. Once adapter sleeve 16 is in position within receptacle 18, a sample tube may be inserted into the adapter sleeve and rack.

To prevent adapter sleeve 16 from moving within its associated receptacle 18, each adapter sleeve and receptacle is provided with locking device 26. Preferably, locking device 26 comprises a bayonet type fitting 28 which includes one or more retaining tabs 30 located within receptacle 18 at a position intermediate to receptacle base portion 22 and receptacle upper portion 24. Each adapter sleeve 16 has a base portion 32 (see FIG. 2) which includes at least one inverted L-shaped slot 34, having a long leg 35 and a short leg 36, for receiving a corresponding retaining tab 30.

Bayonet type fitting 28 further includes a spring for urging adapter sleeve 16 in a direction away from receptacle base 20. Typically, the spring is a coil type compression spring 38, located in receptacle base portion 22. Retaining tab 30 serves the additional purpose of retaining compression spring 38 within receptacle base portion 22.

When adapter sleeve 16 is initially inserted into receptacle 18, it is typically in an unlocked position 40. In this position, adapter sleeve 16 is freely removable from receptacle 18, and compression spring 38 exerts little or no spring force against base portion 32. To lock adapter sleeve 16 into receptacle 18, long leg 35 of L-shaped slot 34 is positioned over retaining tab 30. To aid in this positioning, L-shaped slot 34 may have a chamfer 44 at base portion 32. Adapter sleeve 16 is then pushed in a direction towards receptacle base 20 and compressing spring 38. Retaining tab 30 is guided into long leg 35 of L-shaped slot 34 by chamfer 44. The pushing of adapter sleeve 16 continues until retaining tab 30 is at the junction of long leg 35 and short leg 36 of L-shaped slot 34 (typically about 0.25 inches). At this point, adapter sleeve 16 is rotated about its longitudinal axis, typically about 20 degrees, until retaining tab 30 is at the opposite end of short leg 36. Short leg 36 may include a locking slot 48 extending essentially parallel to long leg 35 for receiving retaining tab 30 when adapter sleeve 16 is in the locked position 50. When adapter sleeve 16 is released, spring 38 pushes up against the adapter sleeve, so that locking slot 48 engages with retaining tab 30, locking the adapter sleeve into position. When an adapter sleeve is removed, the aforementioned procedure is merely reversed. Because the adapter sleeve will be inserted within a corresponding receptacle by about 0.25 inches further when in the locked position, the operator is given positive visual feedback as to the status of the adapter sleeve.

The adapter sleeves are designed to accurately position each sample tube at a predetermined, standardized position within sample rack 12. For example, a sample tube having a diameter of 12 mm and a length of 65 mm, such as the sample tubes made by Sarstedt and sold under the brand name of Monovette Microtainer, would be in the same axially position as, for example, a sample tube having a diameter of 13 mm and a length of 75 mm, such as the sample tubes manufactured by Beckton Dickinson of Rutherford, N.J. and sold under the brand name of Vacutainer with Hemogard Closure, when the sample tubes are used with the appropriate adapter sleeves. In either instance, the sample tube will be concentric with the corresponding receptacle 18.

To compensate for differences in sample tube lengths, each adapter sleeve includes a collar 52, 54. When sample tubes having different lengths are used with the appropriate adapter sleeve, collars 52, 54 position the corresponding sample tube so that the uppermost portion of each sample tube is maintained at the same height relative to receptacle base 20. Stated alternatively, when different sample tubes are each used with an adapter designed for that particular sized sample tube, each sample tube will be concentric with its corresponding receptacle, and each sample tube's septum will be arranged at the same height. In this manner, an associated sampling probe would move to the same x-y-z coordinate position for each sample tube, regardless of sample tube diameter or length. Should a different sample tube that is not supported by the adapter sleeves already within the rack need to be inserted into the sample rack, an operator merely inserts the appropriate adapter sleeve. Thus, because each receptacle may be utilized without regard to the sample tube size, efficiency and flexibility of the associated sampling system is greatly increased.

To help identify the correct adapter sleeve 16 for a particular sample tube, each type of adapter sleeve may be color coded. For example, the adapter sleeve for the aforementioned sample tube having a diameter of 12 mm and a length of 65 mm, may be black in color, whereas the adapter sleeve for a sample tube having a diameter of 13 mm and a length of 75 mm may be yellow. Preferably, the adapter sleeves are molded of a plastic material having the desired color.

Typically, the adapter sleeves, the sample rack and the shuttle tray are each molded of a plastic material by the process of, for example, injection molding. Further, the adapter sleeves, the sample rack and the shuttle tray are each discrete components.

Each receptacle is further provided with an elongated opening or openings 56 located in the receptacle side 58. Each adapter sleeve is likewise provided with an elongated opening or openings 60 located in the adapter sleeve side 62. When adapter sleeve 16 is in locked position 50, receptacle opening 56 corresponds with adapter sleeve opening 60, so that information marked upon a side of a sample tube contained within adapter sleeve 16 can be viewed. For example, a sample tube may have a bar code imprinted on its side, identifying the test to be run and other pertinent information. By aligning up the bar code with elongated openings 56, 60, a bar code reader can easily scan the bar code.

To help keep the information marked on the sample tube aligned up within the adapter sleeve opening 60, and to help keep the sample tube properly positioned within adapter sleeve 16, each adapter sleeve is provided with a gripper 64. Preferably, gripper 64 comprises at least one flexible gripping arm 66 having a free end 68 and a fixed end 70. Flexible gripping arm 66 is accommodated within an elongated arm opening 72 located in adapter sleeve side 62. Preferably, elongated arm opening 72 is positioned approximately 90 degrees from adapter sleeve elongated opening 60. Fixed end 70 is fastened to adapter sleeve side 62 at one end of elongated arm opening 72 so that flexible gripping arm 66 is recessed within arm opening 72. Additionally, flexible gripping arm 66 has an inwardly projecting surface 74 and an outwardly projecting surface 76. Inwardly projecting surface 74 is located intermediate to fixed end 70 and free end 68, and projects into and past the inner peripheral surface 78 of adapter sleeve 16. Outwardly projecting surface 76 is located at free end 68 and is essentially flush with the outer peripheral surface 80 of adapter sleeve 16. When a sample tube is inserted into the appropriate adapter sleeve 16, it pushes against inwardly projecting surface 74, causing inwardly projecting surface 74 to become essentially flush with inner peripheral surface 78, and forcing outwardly projecting surface 76 beyond outer peripheral surface 80. Typically, to prevent binding between outwardly projecting surface 76 and receptacle 18, the adapter sleeve is inserted into the receptacle before the corresponding sample tube is placed into the adapter sleeve. Once adapter sleeve 16 is in position, the appropriate sample tube is inserted, causing outwardly projecting surface 76 and inwardly projecting surface 74 to frictionally engage with receptacle 18 and the sample tube, respectively.

Figure 3:
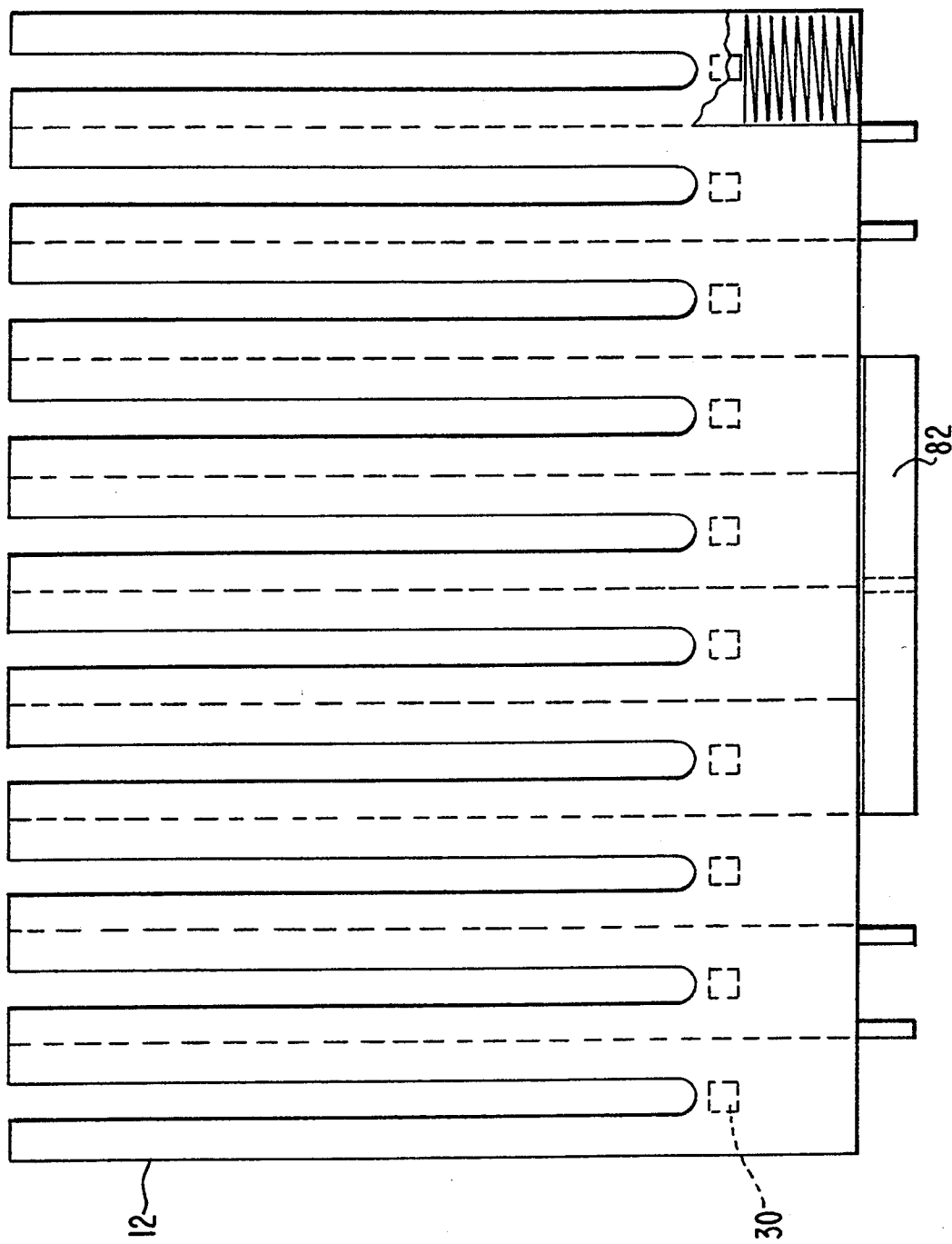
FIG. 3 is a partial sectional elevational view of the sample rack of the present invention.

Referring also to FIGS. 3 and 4, a rotatable rack stand 82 is attached to a base of a rectangular shaped sample rack 12. Rack stand 82 is generally rotatable to two semi-fixed positions. The first position, illustrated in FIGS. 1 and 3, has rack stand 82 being essentially linear with sample rack 12, so that the rack stand can be accommodated within shuttle tray 14. In this position, rack stand 82 acts as a guide, helping to keep sample rack 12 aligned with shuttle tray 14. The second position, illustrated in FIG. 4, has rack stand 82 being essentially perpendicular to sample rack 12. In this position, the rack stand functions as a stand to prevent sample rack 12 from tipping over, when the sample rack is not being used with shuttle tray 14.

FIG. 5 better illustrates shuttle tray 14. Shuttle tray 14, and the mechanism for transporting a plurality of such shuttle trays is disclosed in detail, for example, in U.S. Pat. No. 3,418,084 to Allington.

Briefly, each shuttle tray 14 has complimentary camming surfaces 84 and 86 formed at the opposite ends thereof. A drive mechanism (not shown) comprising gears which mesh with gear tracks 88 on the bottom of the shuttle trays, drives the shuttle trays in the appropriate direction. The shuttle tray drive mechanism causes a driven shuttle tray to push a shuttle tray in front of it and the camming surfaces effect a lateral displacement in the manner described by the above-referenced patent to Allington. The shuttle trays are transported, one behind the other, so that the sample tubes are passed to various stations in the manner described in the above referenced Hulette et al application. Of course, the sample rack can be transported by any method, and the present invention should not be considered constrained by the use of a shuttle tray.

The invention now being fully described, it will be apparent to one or ordinary skill in the art that any changes and modifications can be made thereto without departing from the spirit or scope of the invention as set forth herein.

What is claimed is:

1. A sample rack assembly for holding, transporting and positioning sample tubes comprising:
   a sample rack having a plurality of receptacles for receiving respective sample tubes;
   individual adapter sleeves removably insertable into a respective one of said receptacles, each said adapter sleeve for receiving one corresponding sample tube; and
   locking means for releasably locking each said adapter sleeve in said receptacle.

2. A sample rack assembly as defined in claim 1, wherein said receptacle has a base; and further comprising spring means within said receptacle for urging said adapter sleeve in a direction away from said base.

3. A sample rack assembly as defined in claim 2, wherein said spring means is a coil type compression spring.

4. A sample rack assembly as defined in claim 2, wherein said receptacle has a base portion adjacent to said base, each said spring means being disposed in said base portion.

5. A sample rack assembly as defined in claim 4, wherein said receptacle has an upper portion adjacent to an opposite side of said base portion relative to said base; and further comprising at least one retaining tab for retaining said spring means within said base portion, said retaining tab being disposed intermediate said base portion and said upper portion.

6. A sample rack assembly as defined in claim 5, wherein said locking means comprises said retaining tab.

7. A sample rack assembly as defined in claim 1, wherein said adapter sleeve has a tubular shape having an inner peripheral surface and an outer peripheral surface.

8. A sample rack assembly as defined in claim 7, wherein said adapter sleeve includes gripping means for holding the sample tube.

9. A sample rack assembly as defined in claim 8, wherein said gripping means comprises at least one flexible gripping arm disposed within an opening on a side of said adapter sleeve, said gripping arm having an inwardly projecting surface extending within said adapter sleeve past said inner peripheral surface, and an outwardly projecting surface being essentially flush with said outer peripheral surface.

10. A sample rack assembly as defined in claim 9, wherein said adapter sleeve slidingly receives and engages with a corresponding sample tube, said at least one gripping arm being pushed by the sample tube whereby said inwardly projecting surface frictionally engages with said sample tube and said outwardly projecting surface frictionally engages with said rack.

11. A sample rack assembly as defined in claim 1, and further comprising a shuttle tray for receiving a base of said rack.

12. A sample rack assembly as defined in claim 1, and further comprising a rotatable rack stand connected to a base of said rack.

13. A sample rack assembly as defined in claim 1, wherein said adapter sleeve comprises a plurality of said adapter sleeves forming a set of adapter sleeves, each said adapter sleeve of said set being removably insertable into said receptacle and each adapter sleeve of said set configured for receiving a different sized sample tube, respectively.

14. A sample rack assembly as defined in claim 13, wherein each adapter sleeve of said set has a discrete identifying color.

15. A sample rack assembly as defined in claim 13, wherein each adapter sleeve of said set is molded of a material having a discrete identifying color.

16. A sample rack assembly as defined in claim 13, wherein each adapter sleeve of said set has a collar for positioning an uppermost portion of each different sized sample tube at the same height relative to a base of said sample rack.

17. A sample rack as defined in claim 1, wherein said receptacle has a base portion and an upper portion adjacent to said base portion; and wherein said locking means comprises at least one retaining tab disposed intermediate said base portion and said upper portion.

18. A sample rack assembly as defined in claim 17, wherein said adapter sleeve has a base portion having at least one L-shaped slot for accommodating a corresponding retaining tab.

19. A sample rack assembly as defined in claim 1, wherein said locking means comprises a bayonet fitting.

20. A sample rack assembly as defined in claim 1, wherein said receptacle has a side having at least one elongated opening and said adapter sleeve has a side having at least one elongated opening, said at least one opening of said adapter sleeve and said at least one opening of said receptacle corresponding when said adapter sleeve is fixedly engaged within said receptacle.

* * * * *